United States Patent [19]

Sanchez et al.

[11] Patent Number: 4,959,327

[45] Date of Patent: Sep. 25, 1990

[54] **VECTORS AND METHOD OF *PENICILLIUM CHRYSOGENUM* TRANSFORMATION**

[75] Inventors: Florentina S. Sanchez; Victor R. Susan; Miguel A. P. Soto; Agustin P. A. Ortega, all of Madrid, Spain

[73] Assignee: Antibiotics, S.A., Madrid, Spain

[21] Appl. No.: 9,713

[22] Filed: Feb. 2, 1987

[30] Foreign Application Priority Data

Jan. 31, 1986 [GB] United Kingdom ............... 8602479
Mar. 26, 1986 [GB] United Kingdom ............... 8607502
Jun. 27, 1986 [GB] United Kingdom ............... 8615798

[51] Int. Cl.$^5$ .................. C12N 1/13; C12N 15/01; C12N 15/52; C12N 15/11
[52] U.S. Cl. .................. 435/172.3; 435/69.1; 435/71.1; 435/171; 435/172.1; 435/254; 435/320; 435/935; 530/27; 935/6; 935/9; 935/22; 935/23; 935/27; 935/52; 935/55; 935/56; 935/59; 935/60; 935/66; 935/68
[58] Field of Search ............... 435/69.1, 71.1, 171, 435/172.1, 172.3, 254, 320, 935; 536/27; 935/6, 9, 22, 23, 24, 27, 52, 55, 56, 59, 60, 66, 68

[56] References Cited

PUBLICATIONS

Yelton et al., 1984, *PNAS* 81: 1470–1474.
Van Solinger et al., 1985, *J. Cellular Biochem.* Suppl. 9c, p. 174, Abstr. #1576.
Sanchez et al., (1987), Gene, 51(1):97–102.
Sanchez et al. (1986), Mol. Gen. Genet., 205:248–52.
Penalva et al. (1987), Nucl. Acids Res., 15:1874.
Portela et al. (1985), Virus Research, 4:69–82.
Southern et al. (1982), J. Mol. App. Genet., 1:327–341.
Vara et al. (1985), Gene, 33:197–206.
Hondel et al. (1985), Mo. Genetics of Filamentous Fungi, 29–38.
Miyajima et al. (1984), Mol. and Cell Biol., 4(3):407–414.
Boyer, W. H. et al., "A Complementation Analysis of the Prestriction and Modification of DNA in Escherichia coli"; 41 J. Mol. Biol. 459–472 (A69).
Schechtman, M. G. et al., "Structure of the Trifunctional trp-1 Gene from Neurospora crasse and its Aberrant Expression is Escherichia coli", J. Mol. App. Genet. 83–99 (1983).
Messing, J., "New M13 Vectors for Cloning"; 101 Meth. Enzymol. 20–79 (1983).

Primary Examiner—Richard A. Schwartz
Assistant Examiner—Richard C. Peet
Attorney, Agent, or Firm—Arnold, White & Durkee

[57] ABSTRACT abstract missing

11 Claims, 3 Drawing Sheets pPctrpC1

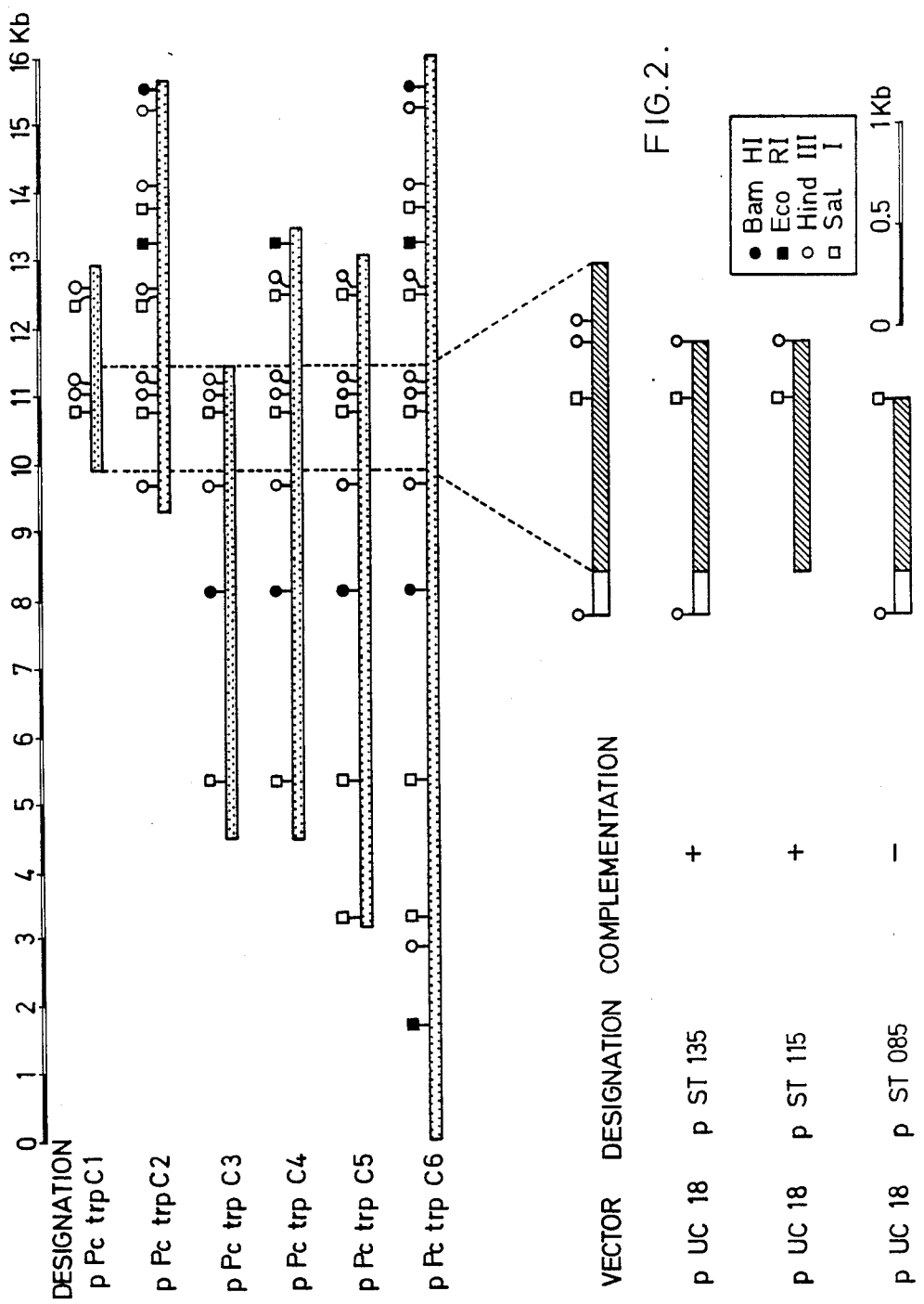

VECTORS AND METHOD OF *PENICILLIUM CHRYSOGENUM* TRANSFORMATION

The present invention relates to *Penicillium chrysogenum*.

BACKGROUND OF THE INVENTION

The ascomycete *P. chrysogenum* is a filamentous fungus that is used for the industrial production of penicillins. Much research has been directed to obtaining high-yielding strains by classical mutagenesis and brute-force selection.

OBJECTS OF THE INVENTION

An object of this invention is to apply the techniques of molecular cloning to. *P. chrysogenum*. More specifically, the present invention is directed to the development of transformation in *P. chrysogenum* with exogenous DNA. with a view to opening up the possibilty of employing genetic engineering to obtain high-yielding penicillin-producing strains of *P. chrysogenum*.

SUMMARY OF THE INVENTION

The present invention provides for the use of auxotrophic mutants of *P. chrysogenum* as receptors for exogenous DNA. The auxotrophic mutant lacks a biosynthetic capability of the wild type *P. chrysogenum*. The successful restoration of this biosynthetic capabilty to give a prototroph can be used as a marker for incorporation of exogenous DNA. To this end, the exogenous DNA is one which includes DNA which will complement the existing DNA of the auxotrophic mutant in order to restore the missing biosynthetic capability.

Candidate auxotrophic markers include trorpC, pyr4, argB, and NO$^{-3}$ reductase.

PREFERRED EMBODIMENTS

For example, the present invention provides for the use of biosynthetic genes of wild type *P. chrysogenum* as a way to select and identify clones with incorporated foreign DNA. The exogenous DNA can include DNA of the wild type P. chrysogenum in order to restore prototrophic growth.

By way of example, the marker can be based on the tryptophan biosynthetic pathway genes of wild type *P. chrysogenum*, such as the wild type troC gene. By the present work, we have shown that the biosynthesis of tryptophan in *P. chrysogenum* is similar to that in other filamentous fungi such as *Neurosoora crassa* or *Aspergillus nidulans*, and relies on a multifunctional protein complex. anthranilate synthetase, which also has activities of phosphoribosyl anthranilate isomerase and indole glycerolphosphate synthetase. The trpC gene encodes for a sub-unit of this protein possessing the latter two activities in addition to the glutamine amido transferase activity of anthranilate synthetase.

Thus, in an example of this invention, the mutant is trp$^-$ due to an ineffective trpC gene, and the exogenous DNA complements the existing DNA to restore the trpC gene and give a prototroph.

As a generality, suitable P. chrysogenum DNA from the wild type includes plasmids which can transform the auxotrophic mutant to restore the desired activity. To continue the example of trp$^-$ mutants, the plasmid can be one which restores a wild type trpC gene. Specific plasmids with such capability include plasmids pPpctrpC1 and pPctrpC6 which contain a suitable insert at the single BamHI site of known plasmid PUC13. *Escherichia coli* containing pPctrpC1 and *Escherichia coli* containing pPctrpC6 have been deposited under the Budapest Treaty at the National Collection of Industrial Bacteria, Scotland, on Mar. 14, 1986, and given the respective deposit numbers NCIB 12222 and NCIB 12223.

The plasmids, such as the plasmids pPctrpC1 or pPctrpC6. can themselves be identified bY their ability to comPlement a deficient mutant of *Escherischia coli*, for instance the known trp$^-$ *E coli* mutant trpC9830.

A particularly preferred tryptophan-requiring mutant of *P. chrysogenum* as host strain is the mutant *P. chrysogenum* ATCCI0003 trp2. This strain has been deposited under the Budapest Treaty at the Commonwealth Mycological Institute, England, on Mar. 20, 1986, and given the number CMICC302709.

It is to be noted that the present invention is not limited to restoration of tryptophan biosynthesis in trp *P. chrysogenum* by transformation. Illustrative further examples of auxotrophic mutants include those with defective pvr4, argB, or NO$^{-3}$ reductase genes.

The present invention is illustrated by the following examples, in which reference is made to the accompanying drawings.

SUMMARY OF THE DRAWINGS

FIG. 2 shows restriction enzyme maps of six plasmids obtained in Example 3, along with related information.

EXAMPLES OF THE INVENTION

EXAMPLE 1

Molecular cloning of the trpC gene.

Figure 1:
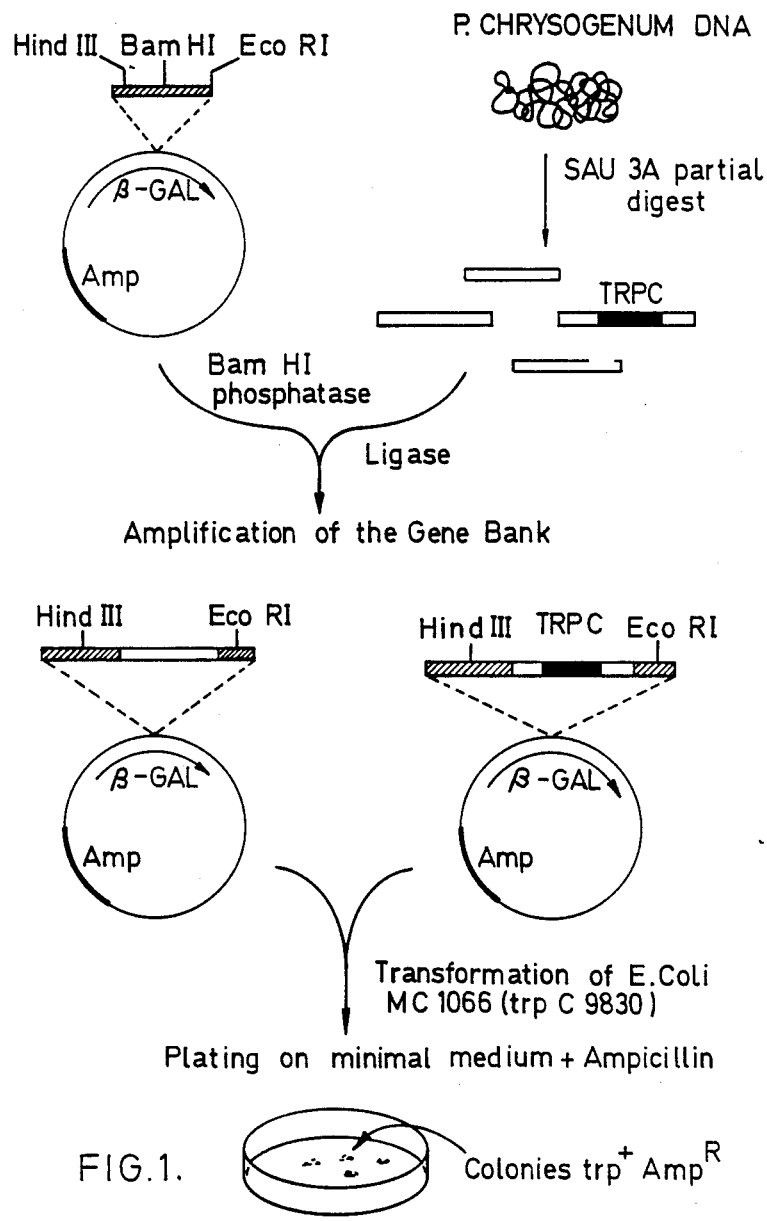
FIG. 1 shows a strategy adopted in Example 1 for cloning the phoshoribosyl anthranilate isomerase-complementing activity of *P. chrysogenum*.

As illustrated in FIG. 1. DNA of *P. chrysogenum* ATCC10003 was partially digested with restriction endonuclease Sau3AI, giving rise to a mixture of fragments with an average size of 5 to 10 Kb. The digestion mixture was layered on top of a 5 to 24% NaCl gradient in 3 mM EDTA at pH 8.0 and centrifuged for 19 hours at 17,000 rpm in an SW40 rotor. The gradient was fractionated and samples of each fraction were analyzed by running them in a 0.8 % agarose gel with standards of suitable molecular weight. The fractions containing DNA fragments of 8 to 10 Kb were pooled, dialyzed against TE buffer (10 mM Tris-HCl, pH 8.0, 1 mM EDTA) and concentrated by ethanol precipitation.

Separately, plasmid pUC13 (Methods in Enzymology (1983) 101, 20–78) was completely digested with BamHI. After inactivation of the enzyme by phenol extraction, the phosphate groups of the 5'-ends were eliminated by treatment with 0.04 units/μg of alkaline phosphatase for 30 minutes at 37° C. in order to prevent self-ligation of the vector. This second enzyme was inactivated by repeated phenol extraction, and the DNA was concentrated by phenol precipitation.

The phosphatase-treated DNA from pUC13 and the P. chrysogenum fragments of 8 to 10 Kb were mixed in a 10:3 molar ratio (vector:insert) and incubated overnight with 6 units of DNA ligase at 14° C. The resultant ligated DNA was used to transform E. coli strainr HB101 (J Mol Biol (1969) 41, 459–472) to ampicillin resistance. A total of 310,000 transformants were obtained. By analysis of a statistically significant number of transformants, it was established that about 60% of the colonies contained recombinant plasmids and that the average insert size was about 8 Kb. The plasmid DNA from these 310,000 transformants was purified by alkaline lysis, followed by CsCl—EtBr equilibrium centrifugation. The purified DNA was stored at −80° C. until use.

The trpC9830 mutation of E. coli strain MC1066 (J Molec Appl Genet (1983 2, 83–99). [lac(IPOZYA)X74, galK, galU, strA, hsdR, trpC9830, leuB6. pyrF74:Tn5(Kmr)]. Was used as host for selection of E. coli trDC by complementation. The amount of DNA employed was high enough to obtain 358,000 transformants with an average insert size of 8 Kb representing 16 times the genome of P. chrysogenum . Cells were plated on selective medium lacking tryptophan. Eleven colonies with the desired phenotype (trp+, ampr) were found after 1 to 9 days of incubation at 37° C. These colonies of insert-containing Plasmids were inoculated in small cultures and the Plasmid DNA was thereby Purified.

Plasmid DNA from these clones was transformed in to E. coli HB101 and selected transformants were grown in large scale culture. The restriction maps for 6 of the Plasmids, designated plasmids pPctrpC1 to pPctrpC6, are show in FIG. 2. All these plasmids complement the phosphoribosyl anthranilate isomerase deficiency when reintroduced in to E. coli MC1066.

The largest insert of 16 Kb is contained in plasmid PPctrpC6. All the inserts in the other Plasmids are contained in plasmid pPctrpC6, and the restriction maps in the overlapping regions are identical suggesting that no cloning artefacts had been generated. Furthermore, genomic clones were isolated from a P. chrysogenum library constructed in lambda EHBL4 using pPctrpC4 as probe. The restriction maps of these phage clones were fully coincident with the plasmid ones in the overlapping regions, showing that the Figure represents the actual configuration of the P. chrysogenum DNA region.

The six plasmids were 32P-labeled by nick translation and hybridized to restriction enzyme digests of P. chrysogenum DNA. The hybridization patterns unambiguously showed the presence of P. chrysogenum DNA inserts.

Figure 3:
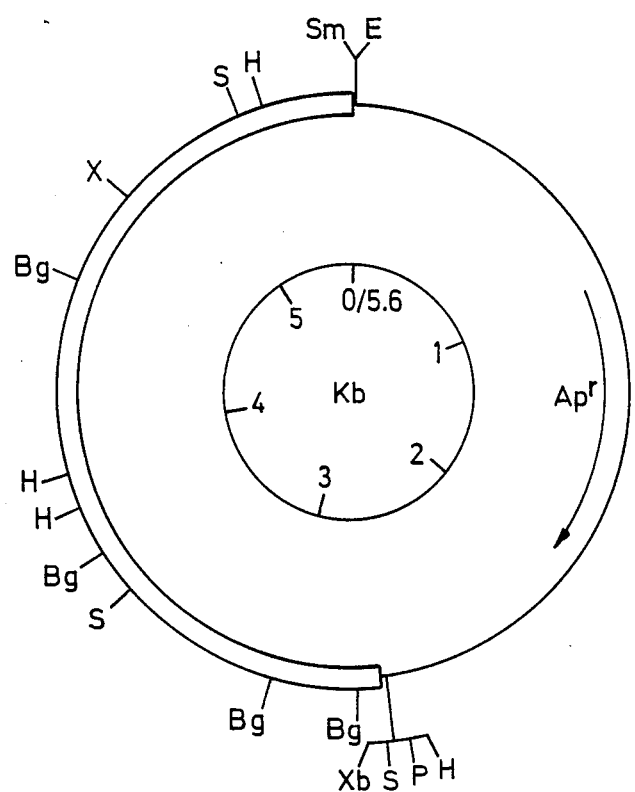
FIG. 3 is a more complete restriction enzyme map for one of the six plasmids of FIG. 2.

A restriction map for plasmid pPctrPC1 is shown in FIG. 3.

EXAMPLE 2

Preparation of P. chrysogenum trp2 mutant

Tryptophan auxotrophs were obtained from spore suspensions of P. chrysogenum ATCC10003 mutagenized with uv light to a survival frequency of about 1% of the initial cell count. Colonies were sPread on complete medium plates supplemented with 250 μg/ml of tryptophan and replicated on minimal medium plates plus or minus the tryptophan. The colonies showing the trp− phenotype were selected for further experiments. All of them grew well in minimal medium plus tryptophan, but did not sporulate unless supplemented with indole (50 μg/ml). One of the mutants, named trp2, was particularly promising for the following reasons:

(1) It grew vigorously when supplemented with tryptophan (250 μg/ml) and sporulated well when supplemented with indole (50 μ/ml).

(2) It did not grow in minimal medium plus anthranilic acid, but did grow in minimal medium supplemented with indole. This is the expected phenotype for mutants lacking phosphoribosyl anthranilate isomerase activity.

(3) It can be transformed to the trp+ phenotype by plasmids which contain at least the genetic information coding for the wild type phosphoribosyl anthranilate isomerase activity of P. chrysogenum.

(4) It had a low reversion frequency to tryptophan prototrophy (less than $10^{-7}$).

EXAMPLE 3

Transformation of P. chrysogenum ATCC10003 trp2 with pPctrpC1 or pPctrpC6

The mutant trp2 from Example 2 was grown in semi-defined medium (0.6% $NaNO_3$, 0.52% $MgSO_4·7H_2O$. 0.52% KCl, 1% glucose, 0.5% yeast extract, 0.5% casamino acid, trace $FeSO_4·7H_2O$. trace $ZnSO_4$). A 1 litre Erlenmeyer flask containing 100 ml of medium was inoculated with $10^7$ spores and incubated at 28° C. for 44 hours. The mycelium was recovered by filtration and washed several times with sterile distilled water. One gram of wet mycelium was resuspended in 10 ml of 1.2M KCl and protoplasts produced by incubation of this suspension with Novozym 234 (20 mg/g mycelium) for 4 to 5 hours with shaking. Protoplasts were separated from mycelial debris by filtration through glass wool and pelleted by low-speed centrifugation.

For transformation, protoplasts are pelleted by centrifugation and resuspended in 10 mM $CaCl_2$, 10 mM Tris-HCl pH 8.0, 1.2 M KCl at $10^9$ protoplasts/ml and incubated for 10 minutes at 30° C. 0.1 ml samples are mixed with 10 μg of plasmid DNA (plasmid pPctrpC1 or pPctrpC6) and 2 ml of 30% PEG 6000 (w/v), 10 mM CaCl2, 10 ml Tris-HCl PH 8.0, 1.2 M KCl, and the mix incubated for 5 minutes at room temperature. After recovery by low speed centrifugation, the protoplasts were resuspended in 1 ml of 1.2M KCl, mixed with 5 ml of osmotically stabilized minimal medium agar maintained at 50° C. and plated on the same medium. Plates were incubated at 28° C. and scored for transformants after 3 to 4 days. Transformants typically aPPeared with a frequency of around 50 transformants/μg of DNA, but only for the plates corresponding to protoplast samples that had been exposed to transforming DNA of the plasmids pPctrpC1 or pPctrpC6.

Tryptophan-plus colonies were then picked up from the selection plates and grown in selective minimal medium. Two types to colonies appeared and maintained their characteristics after several passes through minimal medium. One type of colony was large and similar to wild type in morphology and growth rate. The other colony tyPe had smaller colonies and grew slower. Using Southern blot hybridization with $^{32}P$-labeled plasmid pUC13, it was shown that the trP+ colonies contained transforming DNA. In all clones tested, transformation occurred by integration in to the genome of the recipient, giving high stability of the trP+ phenotype.

EXAMPLE 4

Localizing the trpC complementing activity

The minimal overlapping region of the inserts in plasmids pPctrpC1 to pPctrpC6 is shown in the lower part of FIG. 2. Deletion up to the second HindIII site in the right end of the minimal overlapping sequence (plasmid pST115) did not inactivate the complementing activity, thus localizing this activity in to a 1.15 Kb fragment. However, the SalI-HindIII fragment missing in Plasmid pST085 is essential for complementation. Further nucleotide analysis of plasmid pPctrpC1 localized the intiation of the trpC gene between the SalI and HindIII sites located at the right of the insert.

In further work, we have shown that the Protein encoded bY the DNA insert in plasmid pPctrpCl has the amino acid sequence

```
MADLVDHSPHHATKAAKLASASNVILIDNYDSFTWNIYQYLVLEGATVTVYRNDEVTV
EDLVAKKPTQLVISPGPGHPDTDAGISNAVIKHFSGKVPIFGVMGQQCMITSFGGKVD
VTGEILHGKTSELKHDSKGVYQGLPTSEVTRYHSLAGTHSTIPDCLEVTSRVELGDAS
GKNIIMGVRHKEFAVEGVQFHPESILTQYGRKMFRNFLELTAGTWDNKQGAAVAAPAD
KKLSILDKIYAHRKNAVDEQKKIPALRPEALQAAYDLNIAPPQLSFPDRLQSDYPLSL
MAEIKRASPSKGIISANVCAPAQAREYAKAGASVISVLTEPEWFKGDTIDDLRAVRQS
LEGLPNRPAVLRKEFVFEEYQILEARLAGADTVLLIVKMLDIELLTRLYHYSRSLGME
PLVEVNTPEEMKIAVDLGSEVIGVNNRDLTSFEVDLGTTSRLMDQVPESTIVCALSGI
SGPODVEAYKKEGVKAILVGEALMRAPDTSAFVAQLLGGSNQNFAGASPSSPLVKICG
TRTEEGALAAIQAGADLIGIIMVQGRSRLVPDDVALGISRVVKSTPRPADTLQQPSSA
TSLEWFDHSTNILRHPSRALLVGVFMNQPLSYVVSQQQKLGLDVVQLHGSEPLEWSSL
IPVPVIRKFAPGDIGIARRAYHTLPLLDSGAGGSGELLEESGVKKVLDSDEGLRVILA
GGLNPDNVAGTVKKLGQSGOKVVGLDVSSGVETNGAQDLEKIRAFVKSAKSIRQ.
```

What is claimed is:

1. A method of preparing transformed *penicillium chrysogenum* comprising:
   (a) identifying a *P. chrysogenum* trp⁻auxotrophic mutant having identifying characteristics of ATCC deposited cell line accession number #10003 that is deficient in a tryptophan biosynthetic enzyme;
   (b) transforming the identified *P. chrysogenum* mutant with an exogenous DNA segment which comprises a *P. chrysogenum* trpC gene marker and encodes the tryptophan biosynthetic enzyme which will complement said enzyme deficiency in said mutant to produce a transformed phototrophic *P. chrysogenum*; and
   (c) selecting for the transformed phototrophic *P. chrysogenum* on culture medium lacking the nutrient required by the mutant auxotrophic *P. chrysogenum*; wherein transformed *P. chrysogenum* auxotrophic mutants exhibit restored phototrophy.

2. A method according to claim 1, wherein the auxotrophic mutant of *P. chrysogenum* is cell line ATCC accession number 10003.

3. The method of claim 1 wherein the exogenous DNA segment comprises plasmid pPctrpC1 or pPtrpC6.

4. The method of claim 1 wherein the exogenous DNA segment is incorporated in a plasmid vector, and wherein the exogenous DNA segment includes a gene marker trpC.

5. A method of preparing transformed *Penicillium chrysogenum* comprising:

(a) transforming a *P. chrysogenum* trp⁻ auxotrophic mutant ATCC accession number 10003 deficient in tryptophan enzyme, with an exogenous DNA segment which comprises a *P. chrysogenum* trpC gene marker and encodes an enzyme which will complement said enzyme deficiency in said mutant, to produce a transformed phototrophic *P. chrysogenum*; and
   (b) selecting for the transformed phototrophic *P. chrysogenum* on culture medium lacking the nutrient required by the mutant auxotrophic *P. chrysogenum*; wherein transformed *P. chrysogenum* auxotrophic mutants exhibit restored prototrophy.

6. A plasmid having the identifying characteristics of plasmid pPctrpC1 deposited with the National Collection of Industrial Bacteria having the accession number 12222.

7. A plasmid having the identifying characteristics of plasmid pPctrpC6 deposited with the National Collection of Industrial Bacteria and having the accession number 12223.

8. A Penicillium chrysogenum having the identifying characteristics of a Penicillium deposited with the American Type Culture Collection and having the accession number 10003.

9. A genetically engineered *Penicillium chrysogenum* obtained by introduction of exogenous DNA into a trp⁻ auxotrophic mutant of *P. chrysogenum* having the accession number ATCC 10003, said auxotrophic mutant being deficient in a tryptophan biosynthetic enzyme, and said exogenous DNA comprising a *P. chrysogenum* trpC gene marker incorporated into a plasmid vector, said exogenous DNA complementing said tryptophan biosynthetic enzyme deficiency.

10. The genetically engineered *P. chrysogenum* of 9, wherein the exogenous DNA sequence encodes a protein comprising an amino acid sequence:

```
MADLVDHSPHHATKAAKLASASNVILIDNYDSFTWNIYQYLVLEGATVTVYRNDEVTVEDLV
AKKPTQLVISPGPGHPDTDAGISNAVIKHFSGKVPIFGVMGQQCMITSFGGKVDVTGEILHG
KTSELKHDSKGVYQGLPTSEVTRYHSLAGTHSTIPDCLEVTSRVELGDASGKNIIMGVRHKE
FAVEGVQFHPESILTQYGRKMFRNFLELTAGTWDNKQGAAVAAPADKKLSILDKIYAHRKNA
VDEQKKIPALRPEALQAAYDLNIAPPQLSFPDRLQSDYPLSLMAEIKRASPSKGIISANVCA
PAQAREYAKAGASVISVLTEPEWFKGDTIDDLRAVRQSLEGLPNRPAVLRKEFVFEEYQILE
ARLAGADTVLLIVKMLDIELLTRLYHYSRSLGMEPLVEVNTPEEMKIAVDLGSEVIGVNNRD
LTSFEVDLGTTSRLMDQVPESTIVCALSGISGPODVEAYKKEGVKAILVGEALMRAPDTSAF
VAQLLGGSNQNFAGASPSSPLVKICGTRTEEGALAAIQAGADLIGIIMVQGRSRLVPDDVAL
GISRVVKSTPRPADTLQQPSSATSLEWFDHSTNILRHPSRALLVGVFMNQPLSYVVSQQQKL
GLDVVQLHGSEPLEWSSLIPVPVIRKFAPGDIGIARRAYHTLPLLDSGAGGSGELLEESGVK
KVLDSDEGLRVILAGGLNPDNVAGTVKKLGQSGOKVVGLDVSSGVETNGAQDLEKIRAFVKS
AKSIRQ.
```

11. The genetically engineered *P. chrysogenum* of claim 7, wherein the exogenous DNA segment comprises plasmid pPctrpC1 or pPctrpC6.

* * * * *

UNITED STATES PATENT AND TRADEMARK OFFICE
CERTIFICATE OF CORRECTION

PATENT NO. : 4,959,327

DATED : Sep. 25, 1990

INVENTOR(S) : Florentina S. Sanchez, et al.

It is certified that error appears in the above-identified patent and that said Letters Patent is hereby corrected as shown below:

On the title page, under "[57] ABSTRACT", the statement "abstract missing" should be deleted and insert therefor the following:

Disclosed is a method for transforming *Penicillium chrysogenum*. More particularly, the method includes obtaining an auxotrophic mutant of *P. chrysogenum* and employing an exogenous segment of *P. chrysogenum* DNA capable of complementing said auxotorph so as to restore prototrophy. The exogenous DNA segment thus comprises a phenotypic marker indicating successful transformation of the mutant.

The exogenous complementary DNA segment may further be prepared in a recombinant plasmid vector. These plasmid vectors include, by way of example, the pFctrpCL and pPctrpC$_6$ plasmids developed by Applicants. These transforming plasmid vectors and those having identifying characteristics thereof are suitable for use in the subject transformation process. The exogenous complementary DNA segment comprises a gene encoding a selected biosynthetic enzyme. By way of example, these genes include trpC, pyr4, argB and NO$^{-3}$ reductase, as well as other genes which encode metabolically required enzymes. The most preferred of these is trpC.--

UNITED STATES PATENT AND TRADEMARK OFFICE
CERTIFICATE OF CORRECTION

PATENT NO. : 4,959,327
DATED : September 25, 1990
INVENTOR(S) : Florentina S. Sanchez, et al.

It is certified that error appears in the above-identified patent and that said Letters Patent is hereby corrected as shown below:

| LINE | COLUMN | |
|---|---|---|
| LN 51 | COL 4 | Between the words 'types' and 'colonies', delete the word "to" and substitute therefore -- of --. |
| LN 54 | COL 4 | Delete "tyPe" and substitute therefore -- type --. |
| LN 9 | COL 5 | Delete "bY" and substitute therefore --by --. |
| LN 26 | COL 5 | Delete "penicillium" and substitute therefore -- Penicillium --. |
| LNS 36, 38 | COL 5 | in (b) and (c) delete "phototrophic" and substitute therefore -- prototrophic --. |

UNITED STATES PATENT AND TRADEMARK OFFICE
CERTIFICATE OF CORRECTION

PATENT NO. : 4,959,327　　　　　　　　　　　　　　　Page 3 of 3
DATED　　　: September 25, 1990
INVENTOR(S): Florentina S. Sanchez, et al.

It is certified that error appears in the above-identified patent and that said Letters Patent is hereby corrected as shown below:

| LINE | COLUMN | |
|---|---|---|
| LN 42 | COL 5 | Delete the word "phototrophy" and substitute therefore -- prototrophy --. |
| LN 9 | COL 6 | Delete the word "phototrophic" and substitute therefore -- prototrophic --. |
| LN 36 | COL 6 | Delete " A Penicillium chrysogenum" and substitute therefore -- *Penicillium chrysogenum* --. |

Signed and Sealed this

Twenty-first Day of July, 1992

*Attest:*

DOUGLAS B. COMER

*Attesting Officer*　　　　*Acting Commissioner of Patents and Trademarks*